United States Patent
Potter

(10) Patent No.: US 10,004,712 B2
(45) Date of Patent: Jun. 26, 2018

(54) CONDOM

(71) Applicant: Futura Medical Developments Limited, Guildford, Surrey (GB)

(72) Inventor: Bill Potter, Guildford (GB)

(73) Assignee: FUTURA MEDICAL DEVELOPMENTS LIMITED, Surrey (GB)

( * ) Notice: Subject to any disclaimer, the term of this patent is extended or adjusted under 35 U.S.C. 154(b) by 0 days. days.

(21) Appl. No.: 14/773,076

(22) PCT Filed: Mar. 4, 2014

(86) PCT No.: PCT/GB2014/050629
§ 371 (c)(1),
(2) Date: Sep. 4, 2015

(87) PCT Pub. No.: WO2014/135855
PCT Pub. Date: Sep. 12, 2014

(65) Prior Publication Data
US 2016/0015668 A1    Jan. 21, 2016

(30) Foreign Application Priority Data

Mar. 4, 2013 (GB) .................................. 1303796.5

(51) Int. Cl.
| | | |
|---|---|---|
| *A61K 9/10* | (2006.01) | |
| *A61K 47/02* | (2006.01) | |
| *A61F 6/04* | (2006.01) | |
| *A61K 31/21* | (2006.01) | |
| *A61K 9/00* | (2006.01) | |
| *A61K 9/14* | (2006.01) | |

(52) U.S. Cl.
CPC ................ *A61K 31/21* (2013.01); *A61F 6/04* (2013.01); *A61K 9/0034* (2013.01); *A61K 9/10* (2013.01); *A61K 9/143* (2013.01); *A61K 47/02* (2013.01)

(58) Field of Classification Search
None
See application file for complete search history.

(56) References Cited

U.S. PATENT DOCUMENTS

| | | | | |
|---|---|---|---|---|
| 5,980,477 | A * | 11/1999 | Kelly ................... | A61K 31/765 128/842 |
| 2005/0076917 | A1* | 4/2005 | Wray ........................ | A61F 6/04 128/844 |
| 2009/0197946 | A1 | 8/2009 | Di Bartolomeo | |
| 2009/0272384 | A1* | 11/2009 | Lucas ................ | A41D 19/0055 128/844 |

FOREIGN PATENT DOCUMENTS

| | | |
|---|---|---|
| CN | 103405594 A | 11/2013 |
| JP | 2002165822 A | 6/2002 |
| WO | 02078580 A1 | 10/2002 |
| WO | 03088880 A2 | 10/2003 |
| WO | 2006049627 A1 | 5/2006 |
| WO | 2014020613 A1 | 2/2014 |

OTHER PUBLICATIONS

CIMS ([retrieved from on-line website: https://web.archive.org/web/20110629041053/http://www.mims.com/], publicably available since Jun. 2011).*
Holcberg et al., "Selective vasodilator effect of magnesium sulfate in human placenta", Am J Reprod Immunol. Mar. 2004; 51(3):192-7 (abstract is only attached).*
Bian et al., "Vascular System: Role of Nitric Oxide in Cardiovascular Diseases", Journal of Clinical Hypertension, vol. 10, 2008, pp. 1-10 ([retrieved from on-line website: http://onlinelibrary.wiley.com/doi/10.1111/j.1751-7176.2008.06632.x/full, last visit Mar. 18, 2017]).*
European Patent Office, International Search Report issued in corresponding International Application No. PCT/GB2014/050629, dated Jul. 4, 2014.
Intellectual Property Office, United Kingdom Search Report issued in corresponding Application No. GB1303796.5, dated Jul. 26, 2013.

\* cited by examiner

*Primary Examiner* — Ernst V Arnold
*Assistant Examiner* — Kyung S Chang
(74) *Attorney, Agent, or Firm* — Stites & Harbison, PLLC

(57) ABSTRACT

There is provided a condom having a coating or deposit of a composition which includes a physiologically-active agent such as glyceryl trinitrate, wherein the condom has been treated with a neutralising or acidic material such that the condom, when immersed in water, results in the water having a pH of 7 or less. The condom may be treated with an acidic slurry of dusting powder. Also provided is a process for the manufacture of condoms, in which the process includes the steps of: 1) treating the formed condoms with a neutralising or acidic material; and 2) thereafter applying to the condoms a composition including a physiologically-active agent such as glyceryl trinitrate, wherein the condoms, when immersed in water, results in the water having a pH of 7 or less.

9 Claims, No Drawings

CONDOM

FIELD OF THE INVENTION

This invention relates to condoms and in particular provides a condom having a coating or deposit of a composition incorporating a vasodilator or other physiologically-active agent, in which the storage stability of the active agent is enhanced, thus resulting in an extended shelf-life of the condom.

BACKGROUND TO THE INVENTION

The addition of a composition such as a gel containing glyceryl trintrate (GTN) as vasodilator, as disclosed in WO02/078580, to the inside of the closed end of a condom is of significant benefit to those men who suffer a partial or complete loss of erection due to the reduction of sensation when using a condom. GTN is readily absorbed through the glans penis. Once absorbed, it acts as a vasodilator, promoting blood flow into the penis and so helping such men to maintain a full erection during intercourse when wearing a condom.

A disadvantage of the invention described in WO02/078580 is that GTN is unstable and degrades in contact with natural rubber latex condoms and also condoms made from synthetic rubber latices such as polyisoprene. This instability significantly limits the shelf life of condoms containing compositions including GTN.

It is known from *Chimia*, 58 (2004), 401-408 (Chemical Stability, Compatibility and Shelf Life of Explosives) that the decomposition (ageing) reactions of aliphatic nitrate ester explosives such as GTN can be suppressed by the use of aromatic amines or urea derivatives as stabilisers. Aromatic amines and urea derivatives are basic, from which the skilled person seeking to stabilise GTN in condoms would consider using an alkaline or basic substance. Further, this paper discloses that the radicals and acids present in the reaction mixture auto-catalyse some of the decomposition reactions. This paper also states that the decomposition reactions are catalysed by moisture and residual acids, or by water and acids formed during decomposition. Again, this indicates that decomposition is auto-catalytic under acid conditions. Based on this information, a skilled person would not consider using an acidic substance if he was looking to increase the stability of GTN.

SUMMARY OF THE INVENTION

It is thought that the instability of GTN is caused by the alkaline pH of the condoms. Untreated condoms are generally alkaline due to the materials from which they are made. It has been found that treating the condom to make it neutral or acidic pH increases the stability of GTN. For example, it has now been found that the stability of GTN in contact with condoms can be substantially improved by treating the condoms with a slurry of dusting powder having an acidic pH, that is, a pH below 7. The dusting powder, when dispersed in water, may be acidic or the liquid phase of the slurry may be acidic. Alternatively, the condom may be treated with a neutralising agent to bring the condom to a pH of about 7. The stability of other active agents, such as local anaesthetics, spermicides, topical microbicides and antiviral agents including antiretrovirals, which are also used in condoms and which have a tendency to degradation, thus compromising the shelf-life of the condoms, can also be improved according to the invention.

In one aspect, therefore, the present invention provides a condom having a coating or deposit of a composition which includes a physiologically-active agent, wherein the condom has been treated with a neutralising or acidic material such that the condom, when immersed in water, results in the water having a pH of 7 or less. In this way, the condom carries a neutralising or acidic material.

In another aspect, the present invention provides a condom having a coating or deposit of a composition which includes a physiologically-active agent, in which the condom includes a dusting powder having a pH in aqueous solution or dispersion of less than 7.

In condoms according to the invention that carry a dusting powder, the dusting powder is dry but the reference to the pH of an aqueous dispersion or solution characterises the dusting powder in terms of its suitability for use in the invention. In effect, if the dusting powder were to be removed from the condom and dissolved/dispersed in distilled water (having a pH of 7 before addition of the dusting powder), the resulting dispersion/solution would have a pH of less than 7.

In an alternative embodiment, the dusting powder per se may be pH neutral (or, at least, is not intrinsically acidic) but is dissolved or dispersed in an acidic liquid phase used to treat the condom. This results in the condom having an acidic pH.

The acidic material (e.g. the dusting powder) has a pH in aqueous solution or dispersion of less than 7. Preferably, the material has a pH in aqueous solution or dispersion of less than 6. More preferably, the material has a pH in aqueous solution or dispersion of less than 5.

In some embodiments, the material (e.g. the dusting powder) has a pH in aqueous solution or dispersion in the range 2 to 7. Preferably, the material has a pH in aqueous solution or dispersion in the range 2 to 6. More preferably, the material has a pH in aqueous solution or dispersion in the range 2 to 5. Preferably, the material has a pH in aqueous solution or dispersion in the range 3 to 6. More preferably, the material has a pH in aqueous solution or dispersion in the range 4 to 5.

In some embodiments, the material has a pH in aqueous solution or dispersion in the range 5.5 to 7. Preferably, the material has a pH in aqueous solution or dispersion in the range 6 to 7. The material may have a pH in aqueous solution or dispersion in the range 6.5 to 7. As a result, the condom, when immersed in water, results in the water having a pH of 5.5 to 7, a pH of 6 to 7, or a pH of 6.5 to 7. It has been found that a low pH may cause the burst properties of the condom to deteriorate on ageing. Therefore, in some embodiments, when the material has a pH which is close to neutral so that the alkalinity of the condom is neutralised on application of the material to the condom, the resulting environment is slightly acidic or neutral which can cause a reduction in the deterioration of the burst properties of the condom over time.

In another aspect, the present invention provides a process for the manufacture of condoms, in which the process includes the steps of:
  1) treating the formed condoms with a neutralising or acidic material; and
  2) thereafter applying to the condoms a composition including a physiologically-active agent,
    wherein the condoms, when immersed in water, results in the water having a pH of 7 or less.

In a particular embodiment, the process for the manufacture of condoms includes the steps of:

1A) treating the formed condoms with a slurry of a dusting powder, the slurry having a pH of less than 7; or 1B) treating the formed condoms with an acidic solution followed by treating the condoms with a slurry of dusting powder, such that the dusting powder resulting on the condoms has a pH in aqueous solution or dispersion of less than 7; and 2) thereafter applying to the condoms a composition including a physiologically-active agent.

The physiologically-active agent may, by way of example, be selected from a vasodilator such as GTN, isosorbide mononitrate and isosorbide dinitrate, and pentaerythritol tetranitrate; an anaesthetic, preferably a topical anaesthetic such as lidocaine or benzocaine; and a spermicide, including two or more of such agents.

Where the active agent of the composition comprises a vasodilator, the composition is preferentially applied to the interior surface of the condom at the closed or teat end if intended to assist in the maintenance of erectile function during intercourse when using a condom. If the vasodilator is intended to promote vaginal lubrication, it is preferably located on the outer surface of the condom. In any event, a conventional lubricant is then optionally applied to the condom before packaging.

In the process according to the invention, the acidic material (e.g. the slurry of the dusting powder) has a pH of less than 7. Preferably, the material has a pH of less than 6. More preferably, the material has a pH of less than 5.

In some embodiments, the material (e.g. the slurry of the dusting powder) has a pH in the range 2 to 7. Preferably, the material has a pH in the range 2 to 6. More preferably, the material has a pH in the range 2 to 5. Preferably, the material has a pH in the range 3 to 6. More preferably, the material has a pH in the range 4 to 5.

The slurry containing the dusting powder is preferably aqueous. Optionally the pH may be buffered to minimise any change in the pH of the slurry over the treatment period. For example, the pH of the slurry containing the dusting powder may be buffered in the range 2 to 5, or one of the other ranges described above. Preferably, the treatment is carried out immediately after the condoms are formed by dipping, as is conventionally known in the art, the slurry being used as an alternative to the conventional slurries used in condom manufacture which in general are based on starch, calcium carbonate, magnesium carbonate or silica powders, or mixtures of such powders, which results in the condoms giving an alkaline pH following immersion in water. Alternatively, the condoms can be treated with the slurry containing the dusting powder some time after the manufacturing step, in which case the powder from the conventional slurry is removed during the treatment process.

Preferably, an acidic slurry of insoluble powders is used in the process according to the invention but the treatment can also be carried out in two stages, the condoms being treated with an acidic solution first, and then treated with a slurry of dusting powder, such that the dusting powder resulting on the condoms has a pH in aqueous solution or dispersion of less than 7. In this two stage process, the slurry of dusting powder may be alkaline, neutral or acidic. If the slurry is alkaline, it should only be weakly alkaline such that, when it interacts with the acidic residue provided by the acidic solution applied first, a dusting powder is produced which has a pH in aqueous solution or dispersion of less than 7. Preferably, the slurry of dusting powder has a neutral or acidic pH.

Dusting powders for use in the present invention comprise calcium or magnesium salts of phosphoric or sulphuric acid. Preferably, the dusting powders are calcium or magnesium salts of phosphoric acid. Examples of calcium salts of phosphoric acid include calcium dihydrogen phosphate (Ca$(H_2PO_4)_2$ and calcium hydrogen phosphate (CaHPO$_4$), and mixtures thereof. Magnesium salts of phosphoric acid are available as the mono-, di- and tri-basic salts and examples for use in the present invention include monomagnesium phosphate (magnesium dihydrogen phosphate, magnesium phosphate monobasic) and dimagnesium phosphate (magnesium hydrogen phosphate, magnesium phosphate dibasic), and mixtures thereof. Mixtures of calcium and magnesium phosphates may also be used. Other suitable powders include precipitated and/or fumed silicas and starch. These may be combined with a buffer to minimise any change in the pH of the slurry. The buffer may be an organic acid, such as lactic acid or citric acid, and optionally an alkali metal, preferably sodium, salt of such acid. The pH of the slurry should ideally be maintained below 7, preferably below 5, for the duration of the treatment step of the process and, where a buffer is used, it should have a buffering capacity suitable for this requirement.

Where mixtures of salts are used, ratios of from 0-100% of each ingredient or component may be present, for example from 25-75% of one component and 75-25% of the other (for a two-component mixture). Preferably, calcium dihydrogen phosphate will be present at from 25-100% with the balance (0-75%) being calcium hydrogen phosphate. More preferably, calcium dihydrogen phosphate will be present at from 25-75% with the balance (25-75%) being calcium hydrogen phosphate. In some embodiments, calcium dihydrogen phosphate will be present at from 50-100% with the balance (0-50%) being calcium hydrogen phosphate.

Total powder concentration in the slurry may be from 2-20% mass fraction, preferably 2-16%, more preferably 2.5-10%, even more preferably 3-10%, more preferably still 4-9%, even more preferably 4-8%, more preferably still 5-7%, and in some embodiments about 6%.

In certain embodiments, the total powder concentration in the slurry is preferably 3-16%, more preferably 4-10%, even more preferably 6-10%, more preferably still 7-9%, and in particular embodiments about 8%.

In particular embodiments, there may be a calcium dihydrogen phosphate component of 2-8% and a calcium hydrogen phosphate component of from 0-6%. In other embodiments, there may be a calcium dihydrogen phosphate component of 2-6% and a calcium hydrogen phosphate component of from 2-6%. In further embodiments, there may be a calcium dihydrogen phosphate component of 3-6% (e.g. 4-5%) and a calcium hydrogen phosphate component of from 3-5%. In other embodiments, there may be a calcium dihydrogen phosphate component of 4-8% and a calcium hydrogen phosphate component of from 0-4%. In the embodiments described in this paragraph, the total powder concentration may be 2-20% mass fraction. Preferably, the total powder concentration is 2-16%, more preferably 2.5-10%, even more preferably 3-10%, more preferably still 4-9%, even more preferably 4-8%, more preferably still 5-7%, and in some embodiments about 6%. Alternatively, the total powder concentration in the slurry may preferably be 3-16%, more preferably 4-10%, even more preferably 6-10%, more preferably still 7-9%, and in particular embodiments about 8%.

All percentages relating to powder concentration are mass fraction (equivalent to expressing the amounts as % w/w).

The formulation of slurries for the treatment of dipped latex products is well established in the art. The slurries leave a residue of powder on the latex products, preventing them from sticking together when dried. The slurries typically consist of a dispersion of a suitable powder in water and contain an emulsion of silicone fluid in water stabilised by the addition of a surfactant. Alkali-stable surfactants are typically used. These include anionic surfactants such as the sodium or potassium salts of fatty acids, and fatty sulphates and sulphonates. Non-ionic surfactants such as fatty alcohol ethylene oxide condensation products can also be used, either alone or in combination with anionic surfactants. For the preparation of slurries with pH values below 7, non-ionic surfactants and sulphate and sulphonate anionic surfactants are preferred.

In embodiments in which a neutralising material is used, the neutralising agent neutralises the alkaline pH of the condom. For example, this can be done by converting the sodium or potassium fatty acid salts (which are moderately strongly alkaline) that are present in the condom into insoluble salts (e.g. zinc or magnesium salts) that effectively brings the condom pH down to neutral. For example, the neutralising agent may be zinc and/or magnesium salts such as zinc sulphate and/or magnesium sulphate.

The neutralising material can be soluble. The neutralising material can be dissolved in a liquid which is then used to treat the condom, e.g. by dipping the condom in the liquid in a similar manner to that for a dusting powder slurry. In some embodiments, the neutralising material can be dissolved in the dusting powder slurry.

In one embodiment, a slurry of dusting powder is formed. This slurry may be buffered to an acidic pH, for example, using a citrate buffer. The citrate buffer may be a mixture of trisodium citrate and citric acid. The pH of the slurry may be about 4 to 5. The dusting powder in the slurry may be starch and/or silica. The starch may be present at between 0% and 100% of the dusting powder. The silica may be present at between 0% and 100% of the dusting powder. The starch may be present at between 25% and 75% of the dusting powder. The silica may be present at between 25% and 75% of the dusting powder. The dusting powder content in the slurry may be between 5% and 20% solids, e.g. about 10%. Zinc and/or magnesium sulphate may be dissolved in the slurry. The zinc and/or magnesium sulphate may be present at about 2% w/w.

As mentioned above, condoms produced using traditional methods are generally alkaline which results in the condoms giving an alkaline pH following immersion in water. This is not ideal for the stability of the physiologically-active agent. It is thought that much of the degradation of the physiologically-active agent (e.g. GTN) occurs within the condom rather than at the surface. The present invention aims to at least neutralise the alkalinity of the condom, and in some embodiments, acidify the condom, to improve the stability of the physiologically-active agent. This neutralisation or acidification takes place over the entire condom, e.g. an acidic slurry of dusting powder covers the entire condom, so that the pH of the condom itself (when immersed in water) is changed. The alkaline species present in the condom are converted into a neutral or acid form. Therefore, regardless of where the physiologically-active agent is contained in/on the condom, the neutral/acidic environment will be present. This means that the present invention will provide the required results if the physiologically-active agent is located in the inside of the condom, for example, in the inside of the tip or teat, in an area where other components, such as a lubricant, would not be present.

DETAILED DESCRIPTION OF THE INVENTION

An embodiment of the invention will now be described by way of example.

EXAMPLE 1

A slurry was prepared by dispersing the following materials in water:
1. Calcium dihydrogen phosphate 4.5% mass fraction;
2. Calcium hydrogen phosphate 4.0% mass fraction; and
3. Silicone fluid (added as an emulsion in water stabilised with a non-ionic surfactant) 4.5% mass fraction.

The slurry had a pH of 4.2. Freshly-manufactured condoms straight off the dipping line were treated with the slurry in a batch process for 60 minutes in a washing machine. The slurry was then drained, excess slurry removed by spin drying and the condoms were dried in a tumble drier for 40 minutes at 70° C.

The resulting condoms were dosed with 480 mg of a castor oil-based gel containing 1% GTN. The gel was located in the closed end of the condom. The condoms were then lubricated with 480 mg of silicone fluid (viscosity 350 cS) and sealed in a standard aluminium foil/polyethylene laminate sachet.

Stability of GTN on the treated condoms and standard condoms prepared using the same latex formulation on the same plant but treated with a standard slurry containing 8% mass fraction of starch and 4% mass fraction of silicone emulsion were compared at 40° C. The following table compares the stability of GTN on the calcium phosphate slurry treated condoms and the standard condoms.

| Time at 40° C. (months) | GTN (percent of initial dose) Standard condom treated with with starch slurry | GTN (percent of initial dose) Experimental condom with calcium phosphate slurry |
|---|---|---|
| 0 | 100 | 100 |
| 1 | 70.7 | 92 |
| 2 | 60.4 | 84.1 |
| 3 | 49.5 | 83.1 |

EXAMPLE 2

The above example was repeated except using a slurry prepared by dispersing the following materials in water:
1. Calcium dihydrogen phosphate 4.4% mass fraction;
2. Calcium hydrogen phosphate 3.6% mass fraction; and
3. Silicone fluid (added as an emulsion in water stabilised with a non-ionic surfactant) 4.5% mass fraction.

EXAMPLE 3

The above example was repeated except using a slurry prepared by dispersing the following materials in water:
1. Starch 5% mass fraction;
2. Silica 5% mass fraction;
3. A mixture of trisodium citrate and citric acid to give a pH of 4 to 5—about 2%;
4. 1% zinc sulphate; and
5. 1% magnesium sulphate.

In all the above examples, pH was tested according to the following method. Four condoms as thus treated were immersed in 100 ml water having a pH of 7 in a 150 ml beaker and stirred periodically for 20 minutes at room temperature. The pH of the water was then measured and determined to be less than 7.

The invention claimed is:

1. A condom having a coating or deposit of a composition which includes a physiologically-active agent applied to the condom, the physiologically-active agent comprising a vasodilator, an anaesthetic, and/or a spermicide,
   wherein, prior to applying the coating or deposit of the composition including the physiologically-active agent to the condom, the condom has been treated with a slurry comprising a dusting powder and a neutralizing agent, the slurry having an acidic pH,
   wherein, prior to treating the condom with the slurry, the condom, when immersed in water by itself, results in the water having an alkaline pH, and
   wherein, subsequent to treating the condom with the slurry, the condom, when immersed in water by itself, results in the water having a pH of 5.5 to 7.

2. A condom according to claim 1, in which the dusting powder comprises a mixture of calcium dihydrogen phosphate and calcium hydrogen phosphate.

3. A condom according to claim 1, in which the physiologically-active agent comprises glyceryl trinitrate (GTN) as a vasodilator.

4. A condom according to claim 1, in which the neutralising material is zinc sulphate and/or magnesium sulphate.

5. A condom according to claim 1 having a coating or deposit of a composition which comprises glyceryl trinitrate (GTN), wherein the slurry comprises a mixture of calcium dihydrogen phosphate and calcium hydrogen phosphate.

6. A condom according to claim 1 having a coating or deposit of a composition which comprises glyceryl trinitrate (GTN), wherein the slurry comprises zinc sulphate and/or magnesium sulphate.

7. A condom according to claim 1, wherein the dusting powder is selected from starch and/or silica.

8. A condom according to claim 1, wherein, subsequent to treating the condom with the slurry, alkaline fatty acid salts in the condom have been converted into insoluble salts.

9. A condom according to claim 1, wherein the neutralising material is zinc sulfate and/or magnesium sulfate, and wherein the dusting powder is starch and/or silica.

* * * * *